United States Patent [19]

Fujii et al.

[11] Patent Number: 4,578,216

[45] Date of Patent: Mar. 25, 1986

[54] SHAMPOO COMPOSITION CONTAINING AMINO ACID-ANIONIC AND AMPHOTERIC SURFACE ACTIVE AGENTS

[75] Inventors: Kozo Fujii, Sakura; Takeo Okumura, Funabashi, both of Japan

[73] Assignee: Kao Corporation, Tokyo, Japan

[21] Appl. No.: 677,014

[22] Filed: Nov. 30, 1984

[30] Foreign Application Priority Data

Dec. 21, 1983 [JP] Japan .................. 58-241666

[51] Int. Cl.⁴ .................. C11D 1/10; C11D 1/14
[52] U.S. Cl. .................. 252/542; 252/545; 252/546; 252/547; 252/550; 252/551; 252/555; 252/558; 252/DIG. 13; 252/DIG. 14
[58] Field of Search .............. 252/545, 546, 547, 558, 252/550, 551, 542, 555, DIG. 13, DIG. 14

[56] References Cited

U.S. PATENT DOCUMENTS

| | | | |
|---|---|---|---|
| 3,974,208 | 8/1976 | Dudzinski et al. | 260/501.11 |
| 3,980,769 | 9/1976 | Ghilardi et al. | 424/70 |
| 4,080,310 | 3/1978 | Ng et al. | 252/544 |
| 4,374,056 | 2/1983 | Watanabe et al. | 252/546 |
| 4,478,734 | 10/1984 | Ogino et al. | 252/117 |

FOREIGN PATENT DOCUMENTS

| | | |
|---|---|---|
| 33964 | 10/1973 | Japan . |
| 45607 | 4/1977 | Japan . |
| 106999 | 8/1981 | Japan . |
| 173197 | 10/1983 | Japan . |
| 882635 | 11/1961 | United Kingdom . |

*Primary Examiner*—Prince E. Willis
*Attorney, Agent, or Firm*—Oblon, Fisher, Spivak, McClelland & Maier

[57] ABSTRACT

A shampoo composition comprises an anionic surface active agent, amino acid-type anionic surface active agent, and an amphoteric surface active agent in a specified ratio therebetween. Cationic polymer compounds may optionally be incorporated. The shampoo composition has good detergency as well as foamability and is mild to the skin with good hair conditioning effects.

4 Claims, 1 Drawing Figure

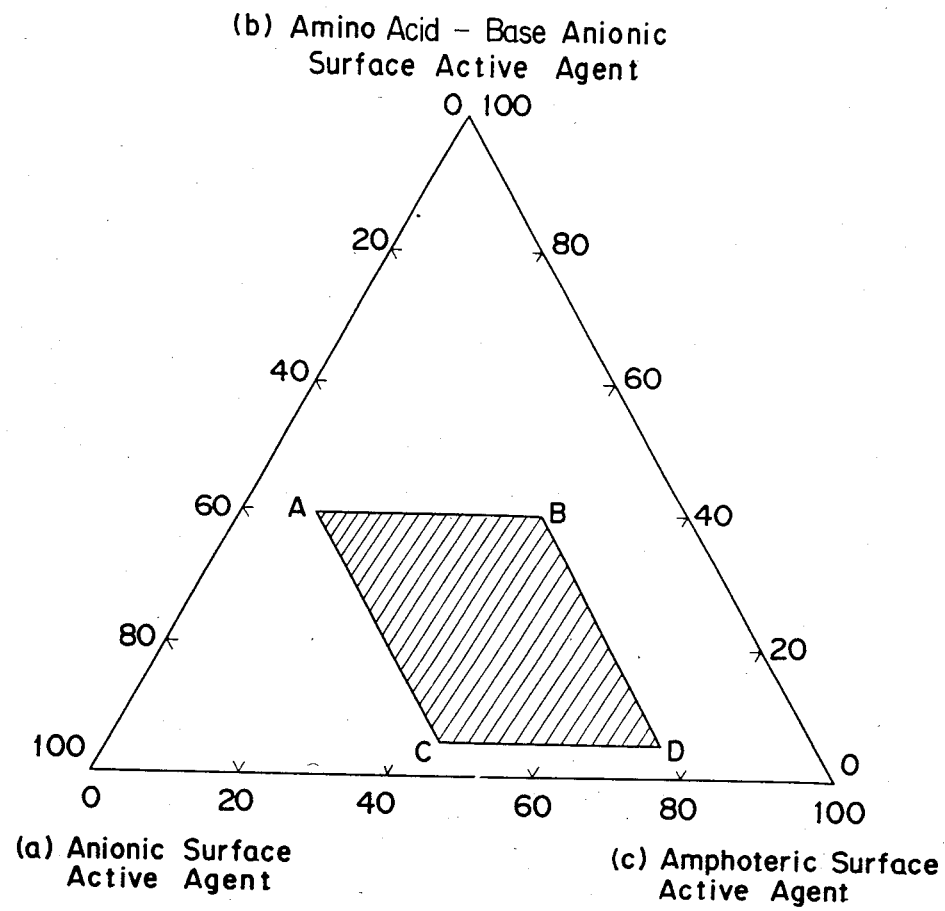
FIGURE

SHAMPOO COMPOSITION CONTAINING AMINO ACID-ANIONIC AND AMPHOTERIC SURFACE ACTIVE AGENTS

BACKGROUND OF THE INVENTION (i) Field of the Invention

This invention relates to shampoo compositions and more particularly, to shampoo compositions which comprise anionic surface active agents, amino acid-type anionic surface active agents and amphoteric surface active agents, and optionally cationic polymer compounds whereby the compositions have good detergency and foamability and are mild to the skin with good hair conditioning effects.

(ii) Description of the Prior Art

Amphoteric surface active agents such as acylated amino acid salts, alkylbetaines, amidobetaines, alkylamidoamine oxides and the like are known as mild surface active agents which are less irritative to hands and skin. However, when used as base for detergents, these surface active agents were found to be short of foamability and detergency upon washing of dirt which is remarkably enriched oil stains, for example, edible oil and fat-deposited plates or dishes or pomade or hair liquid-deposited hair.

Conventional shampoo compositions ordinarily make use of alkyl sulfates or alkylethoxy ether sulfates which exhibit good foamability and detergency but are highly irritative against the skin and hands or eyes. These sulfates are further disadvantageous in that when applied to the hair which has been chemically treated such as by dyeing or cold perming, the sulfates serve to lose the surface smoothness of the hair, thus lowering good texture of the hair after washing.

SUMMARY OF THE INVENTION

The present inventors made intensive studies on shampoo compositions which are less irritative to the skin and hands than known shampoo compositions and have good detergency and foamability with high conditioning effects on the hair. As a result, it was found that shampoo compositions obtained by mixing anionic surface active agents, amino acid-type anionic surface active agents and amphoteric surface active agents in specified ratios with or without further mixing of cationic polymer compounds satisfied the above requirement. The present invention is accomplished based on the above finding.

According to one embodiment of the present invention, there is provided a shampoo composition which comprises (a) an anionic surface active agent except for amino acid-type anionic surface active agents, (b) an amino acid-type anionic surface active agent, and (c) an amphoteric surface active agent, the total amount of these three ingredients ranging from 5 to 30 wt% of the composition, the mixing ratios of the three ingredients being within a composition range surrounded by lines plotted between the following points A, B, C and D of ternary composition triangular diagram of a sole FIGURE, A: (a)=50.0, (b)=40.0, (c)=10.0
B: (a)=20.0, (b)=40.0, (c)=40.0
C: (a)=50.0, (b)=5.0, (c)=45.0
D: (a)=20.0, (b)=5.0, (c)=75.0

According to another embodiment of the invention, there is also provided a shampoo composition which comprises, aside from the above composition of the first embodiment, 0.05 to 1 wt% (hereinafter referred to simply as %) of a cationic polymer compound.

BRIEF DESCRIPTION OF THE DRAWINGS

A sole FIGURE is a triangular diagram showing favorable (a), (b) and (c) ingredients of shampoo compositions according to the invention.

DETAILED DESCRIPTION OF THE INVENTION

Anionic surface active agents used as (a) ingredient in the practice of the invention include the following compounds.

(1) Polyoxyalkylene alkyl ether sulfates represented by the general formula (i) or (ii)

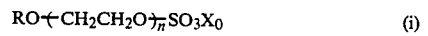

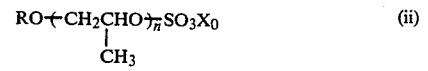

in which R has a linear or branched alkyl group having, on the average, from 8 to 20 carbon atoms, n is a value of from 0.5 to 8 on the average and $X_0$ represents a counter ion.

(2) Alkylsulfate having a linear or branched alkyl group containing from 10 to 20 carbon atoms on the average.

(3) Olefinsulfonates having, on the average, from 10 to 20 carbon atoms in one molecule thereof.

(4) Alkanesulfonates having, on the average, from 10 to 20 carbon atoms in one molecule thereof.

(5) Aliphatic acid salts having a linear or branched and saturated or unsaturated hydrocarbon chain having, on the average, from 10 to 20 carbon atoms.

(6) Alkylethoxycarboxylates having a linear or branched alkyl group containing from 10 to 20 carbon atoms on the average and added with 0.5 to 8 moles of ethylene oxide on the average in one molecule thereof.

(7) Alkyl or alkenylsuccinic acids having an alkyl or alkenyl group containing from 6 to 20 carbon atoms on the average and partially neutralized salts thereof.

(8) Phosphoric acid ester surface active agents represented by the following formula

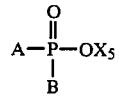

in which A represents

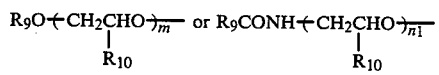

wherein $R_9$ represents a linear or branched and saturated or unsaturated hydrocarbon group, $R_{10}$ represents a hydrogen atom or methyl group, m is a value of from 0 to 6, and $n_1$ is a value of from 1 to 6, B represents $-OX_6$ or A, $X_5$ and $X_6$ independently represent a hydrogen atom or a counter ion.

The counter ion of these anionic surface active agents represented by $X_0$, $X_5$ and $X_6$ includes, for example, ions of alkali metals such as sodium, potassium and the like, alkaline earth metals such as magnesium, ammonium, and alkanolamine bases having 1 to 3 alkanol group containing 2 or 3 carbon atoms such as, for example, monoethanolamine, diethanolamine, triethanolamine, triisopropanolamine and the like.

Of these anionic surface active agents, the compounds of the formulae (1), (2) and (6) are preferred. Most preferably, the polyoxyethylene alkyl ether sulfates represented by the formula (1)-(i) are used.

The amino acid-type anionic surface active agents which are (b) ingredient in the shampoo composition of the present invention include the following compounds.

(1) Amino acid-type surface active agents of the following formula (i) or (ii)

$$X_7OOC-CH_2CH_2-\underset{R_1CO-NH}{CH}-COOX_8 \quad (i)$$

$$R_1CO-\underset{R_2}{\overset{CH_2CH_2COOX_1}{N}} \quad (ii)$$

in which $R_1$ represents an alkyl or alkenyl group having from 7 to 21 carbon atoms, $R_2$ represents a hydrogen atom or an alkyl group having from 1 to 3 carbon atoms, and $X_1$, $X_7$ and $X_8$ independently represent a hydrogen atom or a counter ion.

(2) Amino acid-type surface active agents of the following formula $$R_1CONH\underset{R_{11}}{\overset{}{C}H}-CO(NH-\underset{R_{12}}{\overset{}{C}H}CO)_{\overline{n_1}}-NH\underset{R_{13}}{\overset{}{C}H}-COOX_9$$

in which $R_1$ represents an alkyl or alkenyl group having from 7 to 21 carbon atoms, $R_{11}$, $R_{12}$ and $R_{13}$ independently represent a side chain of amino acid, $n_1$ is a value of from 1 to 6, and $X_9$ represents a hydrogen atom or a counter ion.

The counter ions of these amino acid-type surface active agents represented by $X_1$ and $X_{7-9}$ are alkali metal ions, alkaline earth metal ions, ammonium ion, ammonium ions substituted with an alkyl having from 1 to 3 carbon atoms, alkanolamine bases having a hydroxyalkyl group containing from 1 to 3 carbon atoms, and basic amino acids such as lysine, arginine and the like.

Of the amino acid-type surface active agents mentioned above, N-acyl-N-methyl-beta-alanine or salts thereof of the formula (1)-(ii) in which $R_1CO-$ is an acyl group such as lauroyl, myristoyl, palmitoyl, stearoyl, oleoyl, isostearoyl or the like are preferred. Most preferably, N-lauroyl-N-methyl-beta-alanine and sodium and triethanolamine salts thereof are used.

The amphoteric surface active agents which are used as (c) ingredient of the invention are mentioned below.

(1) Imidazoline amphoteric surface active agents of the following formula $$\begin{array}{c} CH_2-CH_2 \\ | \quad\quad\quad \diagdown \\ \quad\quad\quad\quad\quad N-CH_2Y \\ \quad\quad\quad\quad\diagup | \\ N=\!\!=\!\!=C \quad X_2 \\ | \\ R_3 \end{array} \begin{array}{c} C_2H_4OR_4 \end{array}$$

in which $R_3$ represents an aliphatic acid residue having from 10 to 20 carbon atoms on the average, $R_4$ represents sodium, hydrogen atom or $-CH_2COOX_3$, Y represents $-COOX_3$, $-CH_2COOX_3$ or $$-\underset{OH}{\overset{}{C}H}CH_2SO_3X_3$$

in which $X_3$ represents sodium, a hydrogen atom or an organic base, and $X_2$ represents a hydroxyl group, an acidic salt or anionic surface active sulfate or sulfated compound (2) Amidoamine amphoteric surface active agents of the following formula $$R_5\underset{C_2H_4CO_2X_4}{\overset{}{C}H}-CO\underset{\diagdown}{\overset{\diagup R_6}{N}}\underset{\diagdown R_8}{\overset{\diagup R_7}{C_2H_4N}}$$

in which $R_5$ represents an alkyl or alkenyl group having from 6 to 20 carbon atoms, $R_6$ represents a hydrogen atom, $-C_2H_4OH$ or $-C_2H_4OC_2H_4COOX_4$, $R_7$ represents $-C_2H_2OH$, $-C_2H_4OC_2H_4COOX_4$ or $-C_2H_4COOX_4$, $R_8$ represents a hydrogen atom or $-C_2H_4COOX_4$, and $X_4$ represents a hydrogen atom, an alkali metal, ammonium or organic ammonium.

(3) Alkylamine oxides of the formula (i) and amidoamine oxides of the formula (ii)

$$R_{14}-\underset{R_{16}}{\overset{R_{15}}{\underset{|}{\overset{|}{N}}}}\longrightarrow O \quad (i)$$

$$R_{14}CONH(CH_2)_{\overline{n_2}}\underset{R_{16}}{\overset{R_{15}}{\underset{|}{\overset{|}{N}}}}\longrightarrow O \quad (ii)$$

in which $R_{14}$ represents an alkyl or alkenyl group having from 10 to 20 carbon atoms, $R_{15}$ and $R_{16}$ are the same or different and represent an alkyl group having from 1 to 3 carbon atoms, and $n_2$ is an integer of from 1 to 4.

(4) Alkylbetaines or sulfobetaines of the formula (i) and amidobetaines or amidosulfobetaines of the formula (ii)

$$R_{14}-\underset{R_{18}}{\overset{R_{17}}{\underset{|}{\overset{|}{N^{\oplus}}}}}-(CH_2)_{n_3}X_{10} \quad (i)$$

$$R_{14}CONH(CH_2)_{n_2}-\underset{R_{18}}{\overset{R_{17}}{\underset{|}{\overset{|}{N}}}}-(CH_2)_{n_3}X_{10} \quad (ii)$$

in which $R_{17}$ and $R_{18}$ independently represent an alkyl group having from 1 to 4 carbon atoms, $n_3$ is an integer of from 1 to 3, $X_{10}$ represents $-COO^{\oplus}$ or $-SO_3^{\oplus}$ group, and $R_{14}$ has the same meaning as defined before.

Of the above-mentioned amphoteric surface active agents, the imidazoline and amidoamine amphoteric active agents of the formulae (1) and (2) are preferred.

The cationic polymer compounds which are (d) ingredients of the invention are, for example, polymers of diallyl quaternary ammonium salts, cationic cellulose, cationic starch and cationic vinyl polymers shown below.

(1) Polymers of diallyl quaternary ammonium salts

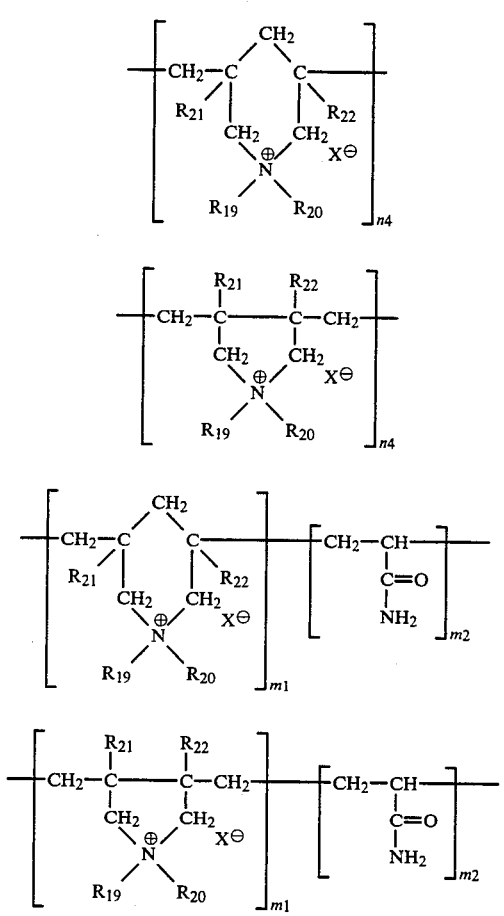

in which $R_{19}$ and $R_{20}$ are the same or different and represent hydrogen or an alkyl group having from 1 to 18, preferably from 1 to 4, carbon atoms, $R_{21}$ and $R_{22}$ are the same or different and represent hydrogen, an alkyl group having from 1 to 3 carbon atoms or a phenyl group, $X^{\ominus}$ represents an anionic residue including a halogen such as chlorine, bromine or the like, an inorganic acid residue such as of sulfuric acid, nitric acid or the like, an organic acid residue such as of methylsulfuric acid, hydroxycarboxylic acid or the like, $n_4$, $m_1$ and $m_2$ are values sufficient to give a molecular weight of 10,000 to 1,000,000.

(2) Cationic cellulose or cationic starch of the formula

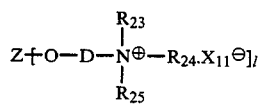

in which Z represents a cellulose or starch residue, D represents an alkylene group or a hydroxyalkylene group, $R_{23}$, $R_{24}$ and $R_{25}$ are the same or different and represent an alkyl group, an aryl group, an aralkyl group or a group capable of forming a heterocyclic ring in combination with the nitrogen atom in the formula $X_{11}^{\oplus}$ represents an anion such as chlorine, bromine, iodine, sulfate, sulfonate, methylsulfate, phosphate or nitrate, and l is a positive integer.

(3) Cationic vinyl polymers of the following formulae

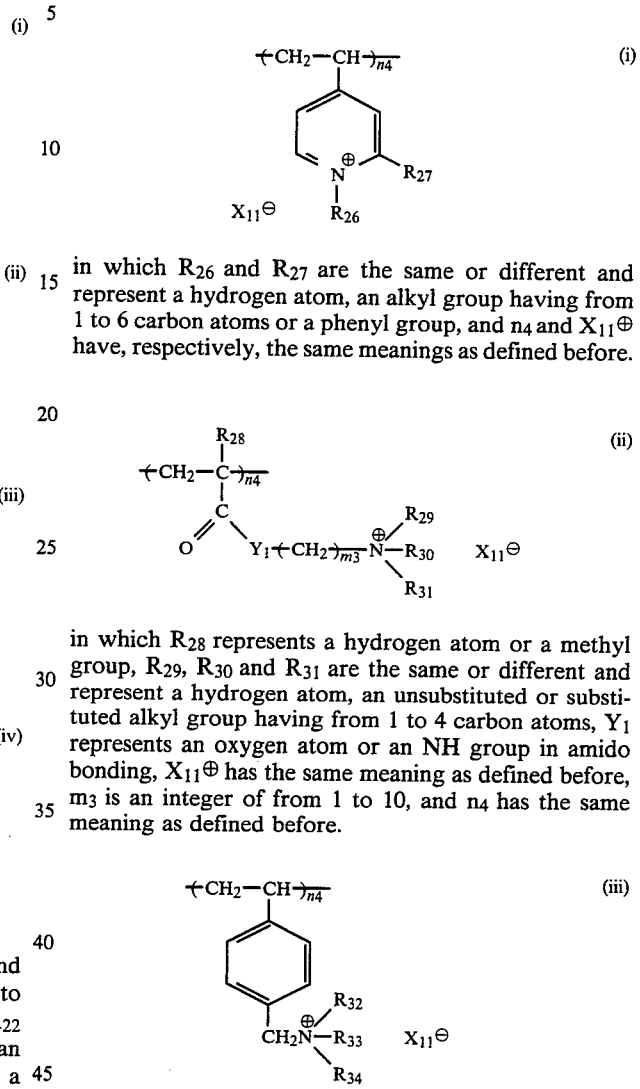

in which $R_{26}$ and $R_{27}$ are the same or different and represent a hydrogen atom, an alkyl group having from 1 to 6 carbon atoms or a phenyl group, and $n_4$ and $X_{11}^{\oplus}$ have, respectively, the same meanings as defined before.

in which $R_{28}$ represents a hydrogen atom or a methyl group, $R_{29}$, $R_{30}$ and $R_{31}$ are the same or different and represent a hydrogen atom, an unsubstituted or substituted alkyl group having from 1 to 4 carbon atoms, $Y_1$ represents an oxygen atom or an NH group in amido bonding, $X_{11}^{\oplus}$ has the same meaning as defined before, $m_3$ is an integer of from 1 to 10, and $n_4$ has the same meaning as defined before.

in which $R_{32}$, $R_{33}$ and $R_{34}$ are the same or different and represent a hydrogen atom and an unsubstituted or substituted alkyl group having 1 or 2 carbon atoms, $X_{11}^{\oplus}$ has the same meaning as defined before, and $n_4$ has the same meaning as defined before.

Of these cationic surface active agents, the cationic cellulose (2) is preferred.

The shampoo composition of the invention should comprise (a) an anionic surface active agent, (b) an amino acid-type anionic surface active agent and (c) an amphoteric surface active agent in the total amount of these three ingredients of from 5 to 30%, preferably from 10 to 25%, of the composition in such a way that the mixing ratios of the ingredients (a), (b) and (c) are within a composition range surrounded by lines plotted between the following points A, B, C and D of ternary composition triangular diagram of a sole FIGURE, in which A: (a)=50.0, (b)=40.0, (c)=10.0
B: (a)=20.0, (b)=40.0, (c)=40.0
C: (a)=50.0, (b)=5.0, (c)=45.0
D: (a)=20.0, (b)=5.0, (c)=75.0

In addition to the above ingredients, the cationic polymer compound (d) may be further added in an amount of 0.05 to 1%, by which the conditioning effect will be further improved.

Other ingredients which may be added to the shampoo composition of the invention include dissolvents such as propylene glycol, glycerine, urea and the like, viscosity modifiers such as ethyl alcohol, isopropyl alcohol, hydroxyethyl cellulose, methyl cellulose, higher alcohols and the like, perfumes, colorants, UV absorbers, antioxidants, preservatives, pearling agents, lotionizing agents, deodorants, antimicrobial substances, anti-seborrheic substances, and horn-solubilizing or softening substances such as sulfur, salicylic acid, enzymes and the like. These substances may be added as desired.

The shampoo composition of the invention may be prepared by successively mixing the ingredients under agitation. Preferably, the shampoo composition should have a pH of from 6 to 8.

The thus obtained shampoo composition is mild to the touch and exhibits good detergency, foamability and conditioning effects on the hair.

The present invention is more particularly described by way of examples, which should not be construed as limiting the present invention.

In examples, the performances are evaluated according to the following methods.

(1) Foaming Test

To an aqueous 1% solution of a shampoo composition was added 0.5% artificial dirt, which was agitated in a cylinder using a flat propeller at 40° C. at 1000 r.p.m. for 5 minutes while reversing the rotation every 10 seconds. Thirty seconds after completion of the agitation, an amount of foams was measured for evaluation.

(2) Detergency Test (A) Artificially soiled cloth

Artificial oily dirt was uniformly dispersed is solvent and cloth(#2003) was contacted with the solution and dried to uniformly deposit the artifical oily dirt thereon. The cloth was cut into 10 cm × 10 cm pieces and used for the test.

(B) Washing conditions and method

A Shampoo composition was dissolved in water of 4°DH to prepare one liter of a 3% shampoo aqueous solution. Five artificially soiled cloth pieces and the shampoo aqueous solution were placed in a stainless beaker for targotometer as they are and agitated in a targotometer at 100 r.p.m. at 40° C. for 10 minutes. The cloth pieces were each rinsed with running water and pressed with an iron for measurement of reflectivity.

(C) Calculation of Detergent Rate

The detergent rate was calculated according to the following equation.

An original cloth prior to washing and a soiled cloth prior to and after the washing was measured by the use of an automatic recording colorimeter (by Shimadzu Seisakusho Co., Ltd.) with respect to reflectivity at 460 mμ and the detergent rate (%) was calculated according to the following equation.

$$\text{Detergent Rate (\%)} = \frac{\text{Reflectivity after Washing} - \text{Reflectivity before Washing}}{\text{Reflectivity of Original Cloth} - \text{Reflectivity before Washing}} \times 100$$

An average of five measurements was used for evaluation.

(3) Conditioning Effect

Hot water of 40° C. was contained in 20 g of a wool texture, to which was applied 1 g of a shampoo composition, followed by crumpling for about 1 minute. Thereafter, the wool texture was rinsed with running water of 40° C. for 30 seconds. The feeling of the shampoo left on the wool texture was organoleptically evaluated according to the following evaluation standard.

Evaluation Standard:
O: Good conditioning effect
Ⓐ: Moderate
Δ: Slight conditioning effect
X: No conditioning effect (4) States of mixture System Immediately after addition of a shampoo composition, the solution system was judged according to the following standard.

Evaluation Standard:
O: Transparent and homogeneous system
Ⓐ: Slightly opaque but homogeneous system
Δ: Opaque system
X: Opaque and separated system The following amphoteric surface active agents were used in the following examples.

Imidazoline

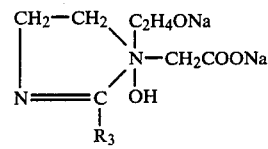

in which $R_3$=alkyl group having from 12 to 14 carbon atoms.

Amidoamine

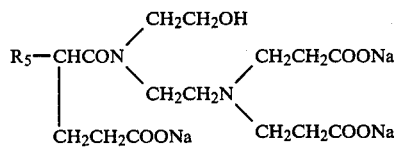

in which $R_5$=alkyl group having from 12 to 14 carbon atoms.

Amidoamine oxide

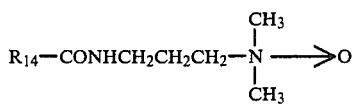

in which $R_{14}$=alkyl group having from 12 to 14 carbon atoms.

EXAMPLE 1

(a), (b) and (c) Ingredients were mixed in a total amount of 15 wt% to prepare shampoo compositions of the following formulations and determined the detergency and foaming strength. The results are shown in Table 1.

(Preparation Procedure)

To a certain amount of water were successively added (a), (b) and (c) ingredients, followed by mixing to obtain a homogeneous composition. After confirmation of the homogeneity, the pH was adjusted to 7 to obtain a transparent liquid shampoo.

TABLE 1

| Shampoo Composition No. | Product of The Invention | | | | | Comparative Product | | | | | | |
|---|---|---|---|---|---|---|---|---|---|---|---|---|
| | 1 | 2 | 3 | 4 | 5 | 6 | 7 | 8 | 9 | 10 | 11 | 12 |
| Composition (%) | | | | | | | | | | | | |
| (a) Sodium Polyoxyethylene lauryl ether sulfate (EO = 2.5) | 7.5 | 3 | 7.5 | 3 | 5.25 | 8.25 | 2.25 | 5.55 | 4.5 | — | 12.0 | 10.0 |
| (b) Sodium N—lauroyl-N—methyl-beta-alanine | 6 | 6 | 0.75 | 0.75 | 3.75 | 3.0 | 3.75 | 0.45 | 6.75 | 7.0 | 3.0 | — |
| (c) Imidazoline (NaCl content 1.1%) | 1.5 | 6 | 6.75 | 11.25 | 6 | 3.75 | 9 | 9 | 3.75 | 8.0 | — | 5.0 |
| Water | balance | balance | balance | balance | balance | balance | balance | balance | balance | balance | balance | balance |
| Evaluation | | | | | | | | | | | | |
| Detergency (%) | 58 | 60 | 56 | 53 | 62 | 45 | 41 | 44 | 42 | 38 | 36 | 42 |
| Foaming Strength (ml) | 130 | 134 | 128 | 125 | 140 | 105 | 98 | 101 | 103 | 79 | 88 | 94 |

\* Indicating the average number of addition moles.
This is also applied to the ensuing examples.

EXAMPLE 2

Ingredients (a), (b) and (c) were mixed in the same manner as in Example 1 to obtain a uniform transparent solution, to which a dispersion of (d) ingredient diluted by water in an amount of 20 times the ingredient was added. After confirmation that a uniform mixture was obtained, the pH was adjusted to 7 to obtain a transparent liquid shampoo. The detergency, foaming strength and conditioning effect of the shampoo were determined with the results shown in Table 2 below.

TABLE 2

| Shampoo Composition No. | Product of The Invention | | | | | |
|---|---|---|---|---|---|---|
| | 13 | 14 | 15 | 16 | 17 | 18 |
| Composition (%) | | | | | | |
| (a) Sodium polyoxyethylene lauryl ether sulfate (EO = 2.5) | 3 | 3 | | | | |
| Sodium polyoxyethylene lauryl ether carboxylate (EO = 2.5) | | | 3 | | | |
| Sodium laurylsulfate | | | | 3 | 3 | 3 |
| (b) Sodium N—lauryl-N—methyl-beta-alanine | 6 | 6 | 6 | 6 | 6 | 6 |
| Potassium salt of acylated coconut fatty acid collagen peptide | | | | | | |
| (c) Imidazoline | 6 | | 6 | 6 | | |
| Sodium amidoamine | | 6 | | | | |
| Amidoamine oxide | | | | | 6 | 6 |
| (d) Cationic cellulose | 0.5 | 0.5 | 0.5 | 0.5 | 0.5 | 0.5 |
| Water | balance | balance | balance | balance | balance | balance |
| Evaluation | | | | | | |
| Detergency (%) | 60 | 55 | 60 | 62 | 58 | 48 |
| Foaming Strength (ml) | 130 | 125 | 130 | 132 | 127 | 102 |
| Conditioning effect | O | O | O | O | O | O |

EXAMPLE 3

Shampoo compositions of the formulations indicated in Table 3 below were prepared in the same manner as in Example 2 to determine detergency, foaming strength, conditioning effect and the state of mixture system. The results are shown in Table 3.

TABLE 3

| Shampoo Composition No. | Comparative Product | Product of The Invention | | | | | | Comparative Product | | Product of The Invention | | Comparative Product |
|---|---|---|---|---|---|---|---|---|---|---|---|---|
| | 19 | 20 | 21 | 22 | 23 | 24 | 25 | 26 | 27 | 28 | 29 | |
| Composition (%) | | | | | | | | | | | | |
| (a) Sodium polyoxyethylene lauryl ether sulfate (EO = 2.5 moles) | 0.8 | 1.0 | 2.0 | 3.0 | 5.0 | 6.0 | 9.0 | 3.0 | 3.0 | 3.0 | 3.0 | |
| (b) Sodium N—lauroyl-N—methyl-beta-alanine | 1.6 | 2.0 | 4.0 | 6.0 | 10.0 | 12.0 | 18.0 | 6.0 | 6.0 | 6.0 | 6.0 | |
| (c) Imidazoline | 1.6 | 2.0 | 4.0 | 6.0 | 10.0 | 12.0 | 18.0 | 6.0 | 6.0 | 6.0 | 6.0 | |

TABLE 3-continued

| Shampoo Composition No. | Comparative Product 19 | Product of The Invention | | | | | Comparative Product | | Product of The Invention | | Comparative Product 29 |
| --- | --- | --- | --- | --- | --- | --- | --- | --- | --- | --- | --- |
| | | 20 | 21 | 22 | 23 | 24 | 25 | 26 | 27 | 28 | |
| (NaCl content 1.1%) | | | | | | | | | | | |
| (d) Cationic cellulose | 0.5 | 0.5 | 0.5 | 0.5 | 0.5 | 0.5 | 0.5 | 0.01 | 0.05 | 1.0 | 1.5 |
| Water | balance | balance | balance | balance | balance | balance | balance | balance | balance | balance | balance |
| Evaluation | | | | | | | | | | | |
| Detergency (%) | 28 | 48 | 57 | 60 | 65 | 66 | 65 | 60 | 59 | 55 | 49 |
| Foaming strength (ml) | 56 | 103 | 125 | 130 | 135 | 140 | 142 | 130 | 128 | 125 | 120 |
| Conditioning effect | O | O | O | O | O | O | O | Δ | O | O | O |
| State of mixture system | X | O | O | O | O | O | X | O | O | O | X |

EXAMPLE 4

Composition:

| | | |
| --- | --- | --- |
| (a) | Sodium polyoxyethylene lauryl ether sulfate (EO = 2.5 moles) | 8 (%) |
| (b) | Sodium N—lauroyl-N—methyl-beta-alanine | 6 |
| (c) | Imidazoline | 6 |
| (d) | Cationic cellulose | 0.3 |
| Coconut fatty acid diethanol amide | | 2.0 |
| Perfume | | 0.3 |
| Preservative | | 0.1 |
| Colorant | | small amount |
| Citric acid | | suitable amount |
| Water | | balance |

A predetermined amount of water was added to a container equipped with an agitator, to which was added sodium polyoxyethylene lauryl ether sulfate and agitated until a uniform solution was obtained. Thereafter, sodium N-lauroyl-N-methyl-beta-alanine was added to the solution and agitated for uniform dissolution, to which was further added imidazoline. To the resulting solution was added a uniform dispersion prepared in a separate container in which coconut fatty acid diethanolamide was heated to about 60° C. and mixed with the preservative, followed by agitating to obtain a uniform solution. When the solution was transparent and uniform, a dispersion of cationic cellulose in water in an amount of 20 times the cellulose was added to the solution. After confirmation of the solution rendered transparent and uniform, the perfume and colorant were added, followed by adjusting the pH to 7 by means of citric acid.

The resulting shampoo composition was tested with respect to detergency, foamability, conditioning effect and low temperature stability, with good results.

EXAMPLE 5

Composition:

| | | |
| --- | --- | --- |
| (a) | Polyoxyethylene stearyl sulfate triethanolamine (EO = 3.5) | 5.0 (%) |
| (b) | Sodium N—lauroyl-N—methyl-beta-alanine | 5.0 |
| (c) | Imidazoline | 10.0 |
| (d) | Cationic cellulose | 0.3 |
| Coconut fatty acid diethanolamide | | 2.0 |
| Perfume | | 0.3 |
| Preservative | | 0.1 |
| Colorant | | small amount |
| Citric acid | | suitable amount |
| Water | | balance |

A shampoo composition was prepared in the same manner as in Example 4.

The shampoo composition had good detergency, foamability and conditioning effect.

EXAMPLE 6

Composition:

| | | |
| --- | --- | --- |
| (a) | Polyoxyethylene lauryl sulfate triethanolamine (EO = 2.5) | 5.0 (%) |
| (b) | Sodium N—cocoyl-N—methyl-beta-alanine | 5.0 |
| (c) | Imidazoline | 10.0 |
| (d) | Cationic cellulose | 0.3 |
| Coconut fatty acid diethanolamide | | 2.0 |
| Perfume | | 0.3 |
| Preservative | | 0.1 |
| Colorant | | small amount |
| Citric acid | | suitable amount |
| Water | | balance |

A shampoo composition was prepared in the same manner as in Example 4.

The shampoo composition had good detergency, foamability and conditioning effect.

EXAMPLE 7

Based on Examples 1 through 6, favorable mixing ratios of (a), (b) and (c) ingredients of the shampoo composition according to the invention were determined. The results are shown in a sole FIGURE.

What is claimed is:

1. A shampoo composition comprising:
   (a) an anionic surface active agent excluding amino acid-anionic surface active agents;
   (b) an amino acid-anionic surface active agent selected from the group consisting of the compounds represented by one of the following formulae:

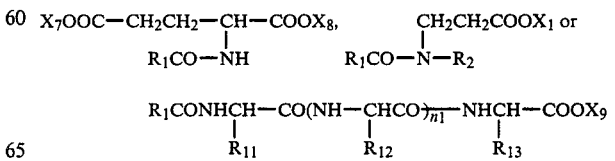

wherein $R_1$ is an alkyl or alkenyl group having from 7 to 21 carbon atoms, $R_2$ represents a hydrogen atom or an alkyl group having from 1 to 3 carbon atoms, and $X_1$, $X_7$ and $X_8$ independently represent a hydrogen atom or a counter ion selected from the group of alkali metal ions, alkaline earth metal ions, ammonium ion, ammonium ions substituted with an alkyl group having from 1 to 3 carbon atoms, alkanolamine bases having a hydroxyalkyl group containing from 1 to 3 carbon atoms, and basic amino acids; and wherein $R_{11}$, $R_{12}$ and $R_{13}$ independently represent a side chain of an amino acid, $n_1$ has a value of from 1 to 6, and $X_9$ represents a hydrogen atom or a counter ion as defined for $X_1$, $X_7$ and $X_8$; and (c) an amphoteric surface active agent selected from the group consisting of a compound having one of the following formulae:

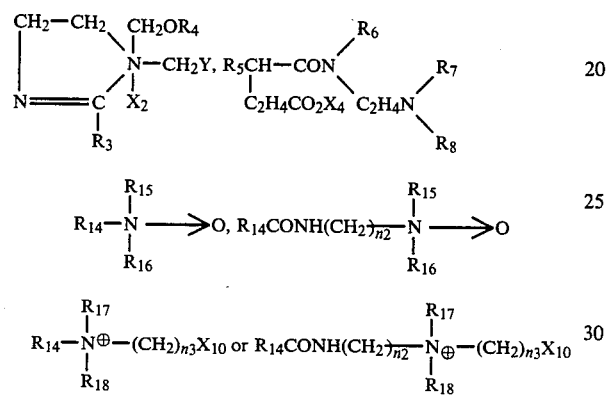

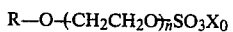

wherein $R_3$ represents an aliphatic acid residue having from 10 to 20 carbon atoms, $R_4$ represents sodium, hydrogen atom or $-CH_2COOX_3$, Y represents $-COOX_3-$ $CH_2COOX_3$ or $-CH(OH)CH_2SO_3X_3$ wherein $X_3$ represents sodium, a hydrogen atom or an organic base, and $X_2$ represents a hydroxyl group, an acidic salt or anionic surface active sulfate or sulfated compound; $R_5$ represents an alkyl or alkenyl group having from 6 to 20 carbon atoms, $R_6$ represents a hydrogen atom, $-C_2H_4OH$ or $-C_2H_4OC_2H_4COOX_4$, $R_7$ represents $-C_2H_4OH$, $-C_2H_4OC_2H_4COOX_4$ or $-C_2H_4COOX_4$, $R_8$ represents a hydrogen atom or $-C_2H_4COOX_4$, and $X_4$ represents a hydrogen atom, an alkali metal, ammonium or organic ammonium; $R_{14}$ represents an alkyl or alkenyl group having from 10 to 20 carbon atoms, $R_{15}$ and $R_{16}$ are the same or different and represent an alkyl group having from 1 to 3 carbon atoms, $n_2$ is an integer from 1 to 4; $R_{17}$ and $R_{18}$ independently represent an alkyl group having from 1 to 4 carbon atoms, $n_3$ is an integer of from 1 to 3, $X_{10}$ represents $-COO^-$ or $-SO_3^-$ group; and wherein the total amount of the three ingredients (a), (b) and (c) ranges from 5 to 30 wt.% of the composition, the mixing ratios of the three ingredients being within a composition range contained by lines plotted between the following points A, B, C and D of the ternary composition triangular diagram as shown in the accompanying figure;

A: (a)=50.0, (b)=40.0, (c)=10.0
B: (a)=20.0, (b)=40.0, (c)=40.0
C: (a)=50.0, (b)=5.0, (c)=45.0
D: (a)=20.0, (b)=5.0, (c)=76.0.

2. The shampoo composition according to claim 1, wherein said anionic surface active agent (a) is at least one member selected from the group consisting of alkylsulfates, polyoxyalkylene alkyl ether sulfates and alkylethoxycarboxylates.

3. The shampoo composition according to claim 2, wherein said polyoxyalkylene alkyl ether sulfates are represented by the following general formula $$R-O-(CH_2CH_2O)_n SO_3X_0$$

in which R represents a linear or branched alkyl group having from 8 to 20 carbon atoms on the average, n is a value of from 0.5 to 8 on the average, and $X_0$ represents an alkali metal, an alkaline earth metal or an alkanolamine which has from 1 to 3 alkanol groups each having 2 or 3 carbon atoms.

4. The shampoo composition according to claim 1, wherein further comprises:

(d) a cationic polymer compound, the total amount of the ingredients (a), (b) and (c) ranging from 5 to 30 wt.% of the composition, wherein the amount of the cationic polymer compound (d) is in the range of from 0.05 to 1 wt.% of the composition.

* * * * *